United States Patent
Street

(10) Patent No.: US 6,516,219 B1
(45) Date of Patent: Feb. 4, 2003

(54) ARRHYTHMIA FORECASTING BASED ON MORPHOLOGY CHANGES IN INTRACARDIAC ELECTROGRAMS

(75) Inventor: Anne M. Street, San Rafael, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 90 days.

(21) Appl. No.: 09/639,313

(22) Filed: Aug. 15, 2000

(51) Int. Cl.[7] ............................................. A61B 5/0452
(52) U.S. Cl. ...................................... 600/515; 600/509
(58) Field of Search ......................... 600/509, 515–518

(56) References Cited

U.S. PATENT DOCUMENTS

| | | | |
|---|---|---|---|
| 4,492,235 A | | 1/1985 | Sitrick ........................ 128/705 |
| 4,546,776 A | * | 10/1985 | Bellin et al. ................. 600/517 |
| 4,680,706 A | * | 7/1987 | Ambos et al. ............... 600/509 |
| 4,893,632 A | | 1/1990 | Armington .................. 128/696 |
| 5,042,497 A | | 8/1991 | Shapland .................... 128/696 |
| 5,522,854 A | | 6/1996 | Ideker et al. ................... 607/6 |
| 5,609,158 A | * | 3/1997 | Chan .......................... 600/518 |
| 5,645,070 A | | 7/1997 | Turcott ....................... 128/702 |
| 5,658,318 A | | 8/1997 | Stroetmann et al. ............ 607/6 |
| 5,718,233 A | | 2/1998 | Selker et al. ................ 128/696 |
| 5,749,900 A | | 5/1998 | Schroeppel et al. ........... 607/4 |
| 5,779,645 A | | 7/1998 | Olson et al. ................. 600/518 |
| 5,842,997 A | | 12/1998 | Verrier et al. ............... 600/518 |
| 5,967,995 A | * | 10/1999 | Shusterman et al. ......... 600/516 |
| 6,058,328 A | * | 5/2000 | Levine et al. ................. 607/14 |
| 6,272,377 B1 | * | 5/2001 | Sweeney et al. ............ 600/515 |

* cited by examiner

Primary Examiner—Kennedy Schaetzle
(74) Attorney, Agent, or Firm—Steven M. Mitchell

(57) ABSTRACT

A method and apparatus for forecasting arrhythmia based on real-time intact intracardiac electrograms. Real-time changes in the electrograms that may be used to predict an impending arrhythmia are identified from non-arrhythmic complexes of the intracardiac electrogram prior to the onset of a spontaneous arrhythmia. One embodiment relies on a running comparison between the morphology of a normal sinus template and a sequence of complexes within a running window. In an alternative embodiment the comparison is made between a pre-arrhythmic template and the acquired electrogram wherein a high correlation is an indicator of an impending arrhythmia. The analysis may be performed continuously or periodically.

13 Claims, 3 Drawing Sheets

ARRHYTHMIA FORECASTING BASED ON MORPHOLOGY CHANGES IN INTRACARDIAC ELECTROGRAMS

TECHNICAL FIELD

This invention relates generally to implantable cardiac therapy devices and ore particularly to the forecasting of the impending onset of a cardiac arrhythmia.

BACKGROUND

Sudden cardiac death (SCD) presents a public health challenge in that often the only indication a patient is at risk appears when the patient succumbs, without warning, to an episode. This is true in part because one major form of SCD is cardiac arrhythmia, typically either ventricular tachycardia that degenerates into ventricular fibrillation, or in some cases spontaneous fibrillation itself. As the underlying physiological causes of cardiac arrhythmias are not fully understood, they cannot be accurately predicted.

Remarkably many victims survive episodes of SCD, either because their arrhythmias spontaneously terminate or because external defibrillation is rapidly implemented. These patients form the bulk of the candidates for implantable cardioverter defibrillators (ICDs). Historically, the hallmark indication for ICD implantation was prior survival of the patient from a confirmed episode of non-sustained tachycardia or fibrillation (in the case of ventricular-based SCD), along with elimination of other possible causes of the arrhythmias. Recently, the size of the target population has also increased due to prophylactic use of ICDs for treatment of SCD based on other risk indicators.

But, in either case, current ICD technology relies on identification and confirmation of an ongoing arrhythmia, primarily based on the sensed heart rate, as opposed to prediction of onset of arrhythmia based on non-arrhythmic conditions, i.e. heart rates below a tachycardia threshold. Previous research into prediction of arrhythmias is abundant but generally directed at risk stratification, that is, statistical prediction of risk over the long-term in a large segment of the population, as opposed to short-term prediction based on the real-time symptoms of a specific individual patient.

In U.S. Pat. No. 5,042,497 (Shapland), incorporated herein by reference, a system for predicting arrhythmias based on sensing neural activity of a patient is disclosed. However, this patent appears to examine only increased arrhythmic risk due to changes in neural tone and provides limited insight into how such a system would be implemented. It would be desirable to provide a predictive method that could be implemented using existing ICD technology and be based on morphology changes of any origin.

SUMMARY OF THE INVENTION

The invention is a method and apparatus for forecasting impending onset of arrhythmia based upon analysis of real-time intact (i,e, non-decomposed) intracardiac electrograms. Real-time changes in the sensed intracardiac electrogram such as changes in morphology that are precursors of arrhythmia are identified in non-arrhythmic complexes of the intracardiac electrogram. The prediction analysis may be performed on a continuous or periodic basis. Other parameters such as heart rate may be used as weighting factors in the analysis. One embodiment of the invention relies on a decrease over time in the degree of correlation between a normal sinus waveform morphology template and the waveform morphology of complexes in a moving window of the intracardiac electrogram to determine whether to forecast an impending arrhythmia. A second embodiment relies on an increase in the degree of correlation over time between a pre-arrhythmic waveform morphology and the waveform morphology of complexes in a moving window of the non-arrhythmic intracardiac electrogram to determine whether to forecast an impending arrhythmia.

DETAILED DESCRIPTION

One aspect of the invention is a method for predicting or forecasting an arrhythmia based on morphology changes over time observed in real-time intact intracardiac electrograms as a precursor of arrhythmia. A change in the morphology of a QRS complex such as changes in the relative area or sequence of peaks in the complex may be predictive of an impending arrhythmia.

The term "intact" as applied to an intracardiac electrogram means that the electrocardiogram signal has not been decomposed into component signals. An example of such decomposition is a Fourier or Karhunen-Loeve Transformation.

The inventive method places few restrictions on the apparatus in which the method is carried out. Therefore, this description primarily presents the method aspects of the invention, but any apparatus and/or system that implements the method aspect is fully within the scope of the invention. Accordingly, because cardiac monitoring equipment typically contains electric or electronic "circuitry," this term includes analog or digital electronics in any combination. Such circuitry is "programmed" or "configured" by including and arranging discrete components or multifunctional components according to well-known principles. "Programming" or "configuring" of electronics can be accomplished using programmable logic arrays, microprocessors, digital signal processors, and other equivalent devices, again by following well-known principles. The only limitations on the apparatus or system aspects of the invention are those specifically recited in the claims.

Figure 1:
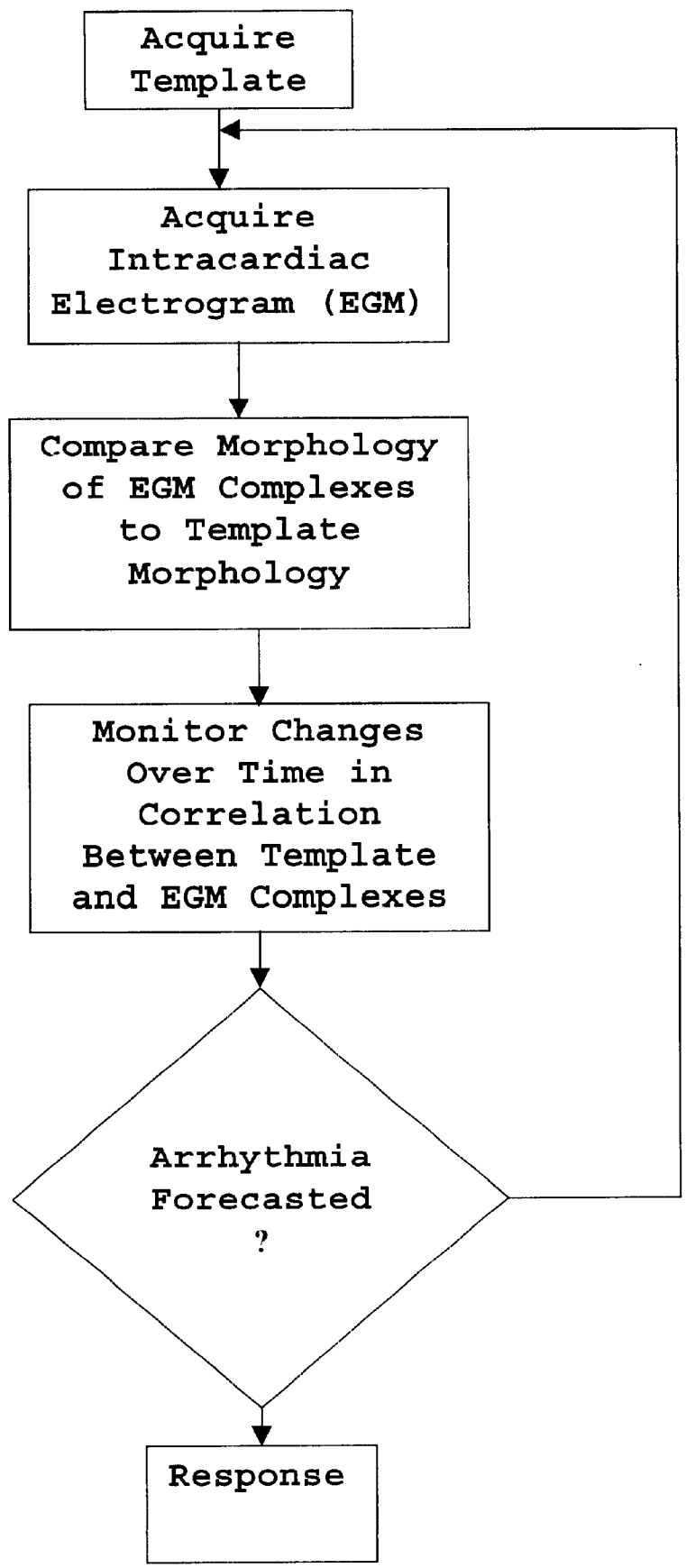
FIG. 1 is a schematic flow chart of one embodiment of the invention.

FIG. 1 is a schematic flow chart of one embodiment of the invention illustrating a method of forecasting spontaneous cardiac arrhythmia. An initial normal sinus rhythm template is acquired in a manner such as disclosed in U.S. Pat. No. 5,779,645 (Olson et al.), which patent is incorporated herein by reference. This may, for example, use a single sinus complex or an average of several complexes. Next, an intact intracardiac electrogram is acquired in a known manner, either continuously or periodically, for example, for periods of about 2 to 10 minutes every hour. In a preferred embodiment, each complex of a running window of, nominally but not limited to, 40 non-arrhythmic complexes is compared to the normal sinus template. A decrease in correlation between the normal sinus waveform morphology and the waveform morphology exhibited in the newly acquired non-arrhythmic complexes in the running window provides a predictor of an arrhythmia.

In an alternative embodiment, the template to which the newly acquired complexes are compared may be a template having a pre-arrhythmic waveform morphology. This pre-arrhythmic template may be acquired or "learned" by the device from previous episodes in the patient. In this embodiment, an increase in correlation between the template waveform morphology and the sensed electrogram waveform morphology constitutes a precursor to arrhythmia.

No matter when or how the template is acquired, the method illustrated in FIG. 1 further comprises a forecast of whether imminent onset of arrhythmia may occur. In this and all other embodiments of the invention, the specific nature or expression of the forecast is not limited to any single format, such as a simple "yes or no," but rather includes such forms as a probability of occurrence within a period of time (e.g., "60% chance within one hour"), or a probability of occurrence that varies with respect to the amount of time before the forecasted event (e.g. "30% chance within one-half hour, 60% chance within one hour, and 90% chance within two hours"), etc.

The morphology of each complex of the window of non-arrhythmic complexes is compared to the template. Based on this comparison, a morphology-determined parameter value (a "score") is assigned to each complex in the window of non-arrhythmic complexes. Next, the method determines whether each complex, based on its determined score, exhibits a "passing score". This is done through the use of one or more threshold values. The second threshold may be applied to exclude from comparison certain complexes such as ones determined to be premature ventricular contractions (PVCs). The set of complexes is now described as a series of pass/non-pass events, possibly with some complexes excluded from consideration. A composite score for the window is computed as each new complex is sensed to provide a measure of the time varying degree of correlation. This time-varying correlation is then evaluated and imminent onset of spontaneous arrhythmia is forecasted if the time-varying correlation calculation falls below a certain value, in the case that the template is an expected normal sinus template, or reaches a certain value, in the case that the template is an expected pre-arrhythmic template.

In an alternative embodiment of the invention, a weighting scheme may be used in which the pass/non-pass demarcation maybe replaced by a metric of the heart rate interval immediately preceding each complex. As an example, but not limited to, the case where a complex that passes and exhibits a good match with the template, its score of "1" is multiplied by the preceding interval. Alternatively, the score of "1" could be multiplied by the inverse of the preceding interval or by the acceleration of the preceding interval relative to the beat prior. There are various alternative responses suitable for use with any of the previously described embodiments of the invention. The alternatives include issuing a pre-arrhythmia warning; preparing for treatment of arrhythmia (e.g., charging a capacitor; storing data); and preventing arrhythmia (e.g., pacing or stimulating a portion of the autonomic nervous system such as the vagus nerve). Each of these alternatives may be carried out in any well-known manner, and the details of such do not limit the scope of the invention. Similarly, without limiting the scope of the invention, each of these alternatives may be combined with one or more of the other alternatives in any appropriate sequence or combination.

In another alternative embodiment of the invention, the morphology comparison may be performed using phase space plots of the waveforms such as is described in U.S. Pat. No. 5,645,070 (Turcott), which patent is incorporated herein by reference. Additionally, the morphology comparison may be performed on features of a waveform complex other than the QRS such as the T wave or the ST segment.

While it is preferred that the method of the invention be implemented on a continuous basis, it may be desirable for power consumption reasons to only operate it periodically, such as once an hour, or that it be triggered such as by a rapid heart rate that is below a tachycardia threshold or the occurrence of one or more PVCs.

Figure 2:
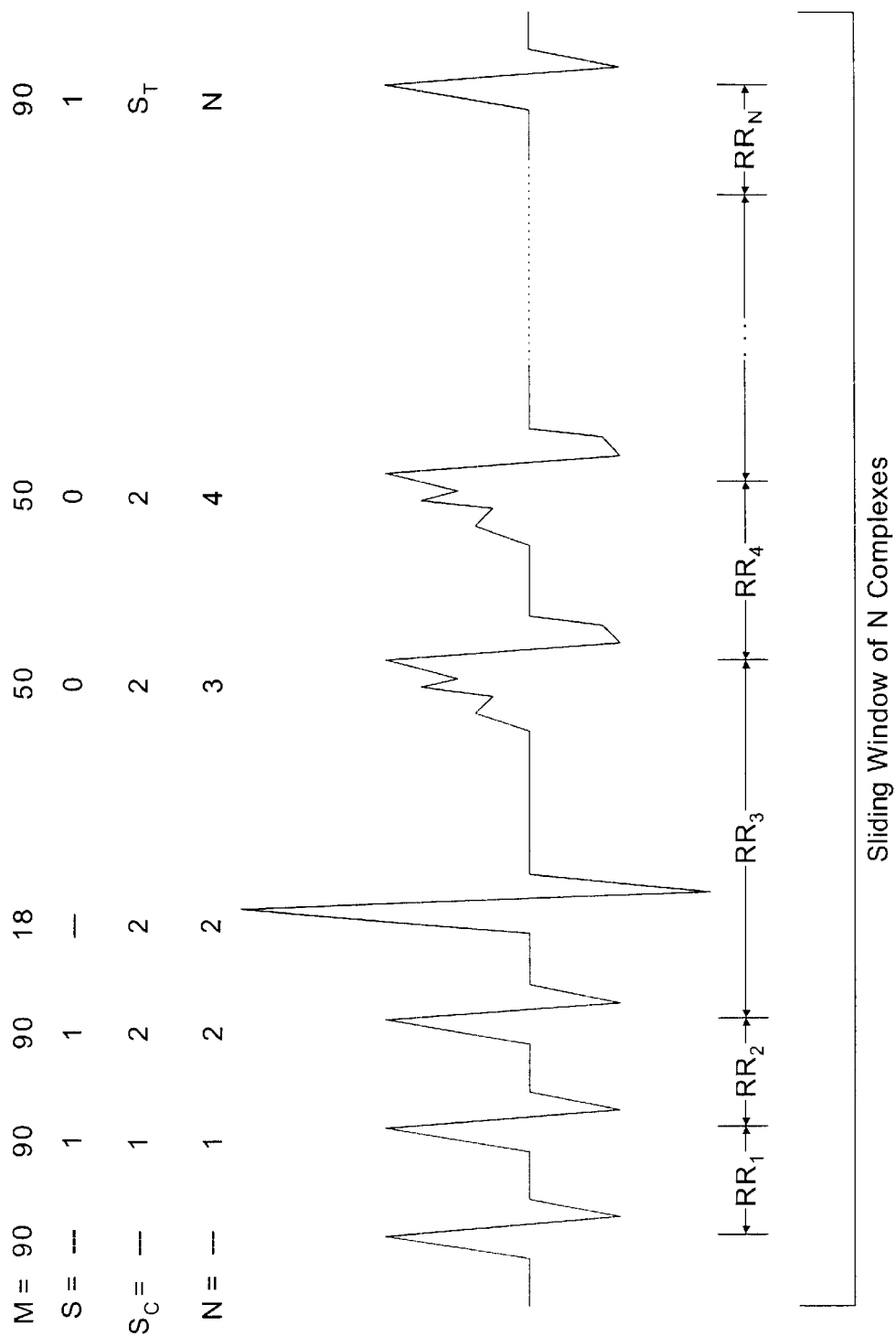
FIG. 2 is a schematic diagram of a real-time intracardiac electrogram in the context of the invention.

FIG. 2 is a schematic diagram of a real-time intracardiac electrogram in the context of the invention. A conventionally used label of the form $RR_x$, where x indicates the $x^{th}$ complex, taking a first non-arrhythmic complex as a reference point, identifies each of the QRS complexes. It should be emphasized, however, that the inventive method is not necessarily based on measurements of the duration of such "R-R intervals" as they are commonly known.

Each of the complexes is compared to the template and is given a morphology score indicated as M. For example, the M value of the first complex is ninety, that of the second complex is ninety, and that of the third complex is eighteen, in a system in which a complex having a morphology that does not correlate at all with a normal sinus template is given a score of zero and a complex that correlates perfectly is given a score of one hundred.

The inventive method assembles a sliding window of complexes, N in number as shown in FIG. 2, and considers each complex in turn. The morphology score, M, is used to determine the count of complexes within the window that are considered to be highly correlated to the template. Complexes that have a score less than a lower threshold value may be removed from the analysis entirely, as being cardiac events that are of atypical origin for non-arrhythmic complexes (for example, PVC's). These complexes do not even contribute as members of the N complexes required to comprise a window. Of the remaining complexes that do comprise the window, only complexes that have a score above an upper threshold value contribute to the count of correlated complexes. The contribution of each complex which is a good match to this count is the S value shown for each complex.

In the case of the complexes shown in FIG. 2, the upper threshold value for the morphology value M is set to be eighty and lower threshold value (for PVC rejection) is set to be thirty. Thus, the first complex has a passing score (M=90>80) and contributes a count of S=1. The second complex also has a passing score (M=90>80) and contributes another count of S=1. The third complex is typical of a premature ventricular contraction (PVC) that does not correlate well with a normal sinus template, so it scores only eighteen and therefore is not even included as a member of the N complexes in the sliding window.

The fourth and fifth complexes score only fifty each; because this is above the lower threshold value of thirty but fails to exceed the upper threshold score of eighty, they are included as members of the set of N complexes but contribute S=0 to the count. This process continues until the $N^{th}$ complex, which scores ninety and contributes another passing count of S=1. A summation of the S values for the window is made to generate a total $S_T$.

As the sliding window advances, it considers a new set of N complexes each iteration, changing its underlying membership each time by one complex. The value of $S_T$ is recalculated each time the window is advanced. This time-varying value is a measure of how many of the total non-arrhythmic complexes considered are the good matches or highly correlated complexes. If this value decreases, it indicates that the intact electrocardiogram comprises a decreasing proportion of correlated complexes, even though the rhythm is non-arrhythmic based on the measured heart rate.

As mentioned above, the heart rate may be used to influence the score such that, for example, complexes that are good matches and follow a long RR interval influence the running score by a greater amount. Such a calculation could be performed using the following equation:

$$S_T = \frac{\sum_{j=1}^{N} RR_j \cdot S_j}{\sum_{j=1}^{N} RR_j}$$

Alternatively, the inverse of the preceding RR interval may be used to provide maximal weighting to morphology changes following short RR intervals. Such a calculation could be performed using the following equation:

$$S_T = \frac{\sum_{j=1}^{N} (1/RR_j) \cdot S_j}{\sum_{j=1}^{N} 1/RR_j}$$

Figure 3:
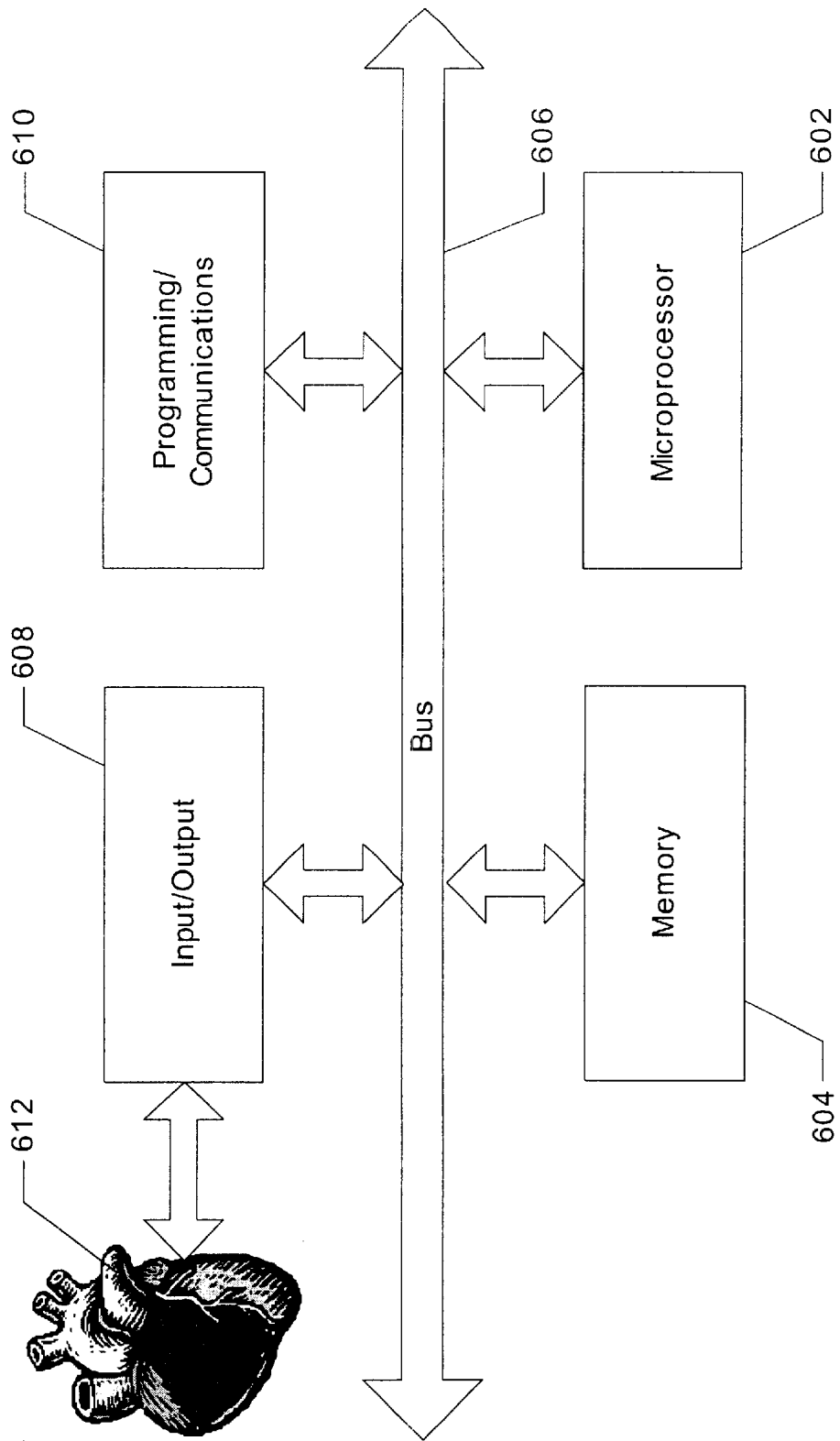
FIG. 3 is a schematic representation of one implementation of any of the various embodiments of the invention.

FIG. 3 is a schematic representation of one implementation of various versions of the invention, comprising a microprocessor 602, memory 604 (which may be any suitable combination of random access memory, or RAM; read-only memory, or ROM; on-board or off-board cache memory associated with microprocessor 602, etc.), bus 606; input/output unit 608; and programming/communications interface 610.

The invention is implemented in software stored in memory 604 and executed by microprocessor 602. Bus 606 permits communication between RAM 604, microprocessor 602 and input/output unit 608. Input/output unit 608 is also coupled to a patient's heart 612 in a well known manner to collect the intracardiac electrogram and (if so configured), deliver one or more antiarrhythmic therapies such as pacing, cardioversion, defibrillation, and the like. (Heart 612 also schematically represents the autonomic nervous system that would be stimulated if such an antiarrhythmic therapy were used alone or in combination with other therapeutic choices). Programming/communications interface 610 is used for downloading stored data to an external programmer and for receiving telemetry from the programmer to modify programmable parameters and/or change the device operating software.

The electrogram and the arrhythmia forecasted may be either atrial or ventricular in any combination, i.e., an atrial electrogram may lead to forecasting either an atrial or ventricular arrhythmia (or both), just as a ventricular electrogram may lead to forecasting either an atrial or ventricular arrhythmia (or both).

Microprocessor 602 instructs input/output unit 608 to collect an intracardiac electrogram, which is then transmitted over bus 606 to microprocessor 602 for immediate processing or to memory 604 for storage and subsequent processing as appropriate. Microprocessor 602 following programming resident in memory 604 identifies non-arrhythmic complexes of the electrocardiogram and determines whether an indicator of imminent arrhythmia is present. If an indicator of imminent onset of arrhythmia is present, microprocessor 602 instructs the system to carry out whatever option is desired, by transmitting therapeutic commands over bus 606 to input/output unit 608.

EXAMPLE

Intact cardiac electrograms were selected from a library of data gathered from fourteen patients in whom an implantable cardioverter defibrillator (ICD) had been implanted and who had subsequently suffered from a total of fifty-two episodes of device-identified events of (suspected or actual) spontaneous onset of ventricular arrhythmia. The ICD had stored and subsequently downloaded the real-time electrograms that preceded each event. Thus, the stored electrograms were available for analysis, as if they had been processed in real time as described below, without any limitation on the scope of the invention.

An electrogram template, essentially as described in U.S. Pat. No. 5,779,645 (Olson et. al.), was created for each patient. A morphology-determined parameter value (corresponding to one hundred minus the morphology "score" as defined in that patent) was determined for all QRS complexes leading up to the onset of a spontaneous ventricular arrhythmia. Sliding windows were created, varying in size from ten to ninety complexes. Within each window, the percentage of time was tracked that the morphology score was above a selected value (evaluated varying between seventy and ninety). If this percentage of time dropped below a threshold value, a warning of impending arrhythmia was issued. The data was evaluated against a threshold that varied between thirty and eighty.

Most warnings occurred within two to three minutes before the onset of the arrhythmia. Because the data was derived from recordings that were only three and one-half minutes in duration, the exact time at which each warning would have first appeared in a continuously monitored real-time electrocardiogram of infinite prior duration is not known from this data. However, this is only a limitation of the data actually used in this example and is not a limitation on the scope of the invention, especially as the invention would be implemented in a future embodiment specifically designed to exploit the advantages of this invention.

To evaluate the specificity of this data set, it was compared to control recordings taken from each patient during patient follow-up examinations. The results appear below. PVC's were included in the non-arrhythmic complexes comprising the sliding window. No weighting scheme was used. The table below shows the specificity and sensitivity as a function of Percent Time Passing

| Percent Time Passing | Window Size (N) | Morphology Score to Pass | Sensitivity | Specificity |
| --- | --- | --- | --- | --- |
| 30 | 90 | 70 | 25% | 95% |
| 60 | 90 | 70 | 73 | 77 |
| 80 | 90 | 70 | 77 | 54 |

Maximum Sensitivity=51/52 episodes=98%

Minimum False Positive Rate (FPR)=0/22 controls

Maximum Specificity (1--FPR)=22/22 controls=100%

Performance optimization defined as (Sensitivity−False Positive Rate)$_{max}$ occurred when Percent Time Passing=60% Window Size (N)=90 and Morphology Score required to Pass=70

Yielded Sensitivity=73% and Specificity=77%

There are two immediate conclusions supported by the data. First, there is a clear correlation between the issuance of a warning before the device-indicated onset of arrhythmia and the subsequently confirmed actual occurrence of arrhythmia. Thus, the method employed to trigger the warning, as described above, successfully identified a real-time precursor of arrhythmia in a non-arrhythmic complex of a intact intracardiac electrogram. This shows that this invention can be used prospectively to accurately forecast spontaneous cardiac arrhythmia in individual patients.

Second, lower values for the nominal threshold ("Percent Time Passing" parameter) indicate that greater variability in the morphology comparison may be permitted before giving a warning of impending onset of arrhythmia and a higher value indicates that less variability would need to be present before a warning was issued. Thus, higher threshold values would be appropriate for initiating relatively more benign therapies, such as antitachycardia pacing or vagal nerve stimulation. Lower threshold values would be more appropriate for initiating aggressive therapies, because the lower threshold values have a greater degree of specificity.

I claim:

1. A method for predicting the onset of an arrhythmia comprising the steps of:
    a. acquiring a normal sinus template representative of the morphology of an electrogram complex during normal sinus rhythm;
    b. acquiring an electrogram including a plurality of non-arrhythmic complexes;
    c. comparing the morphology of the non-arrhythmic complexes to the template; and
    d. deriving an indication of an impending arrhythmia as a function of the comparison between the plurality of non-arrhythmic complexes and the template.

2. The method of claim 1, wherein the plurality of non-arrhythmic complexes comprises a moving window such that as each new complex of the electrogram is acquired the oldest complex of a defined number of complexes in a sequence is removed from the sequence.

3. The method of claim 2, wherein said step of deriving an indication of an impending arrhythmia includes the step of calculating a parameter which is a summation of the results of each morphology comparison of the complexes within the window.

4. The method of claim 1, wherein the result of each morphology comparison is modified by a weighting factor.

5. The method of claim 4, wherein the weighting factor is a function of the duration of an immediately preceding inter-beat interval.

6. The method of claim 1, further including the step of determining if each complex is a premature ventricular contraction (PVC) and if it a complex is determined to be a PVC ignoring such complex for the comparing step.

7. A method for predicting the onset of an arrhythmia comprising the steps of:
    a. acquiring a pre-arrhythmia template representative of the morphology of an electrogram complex prior to an arrhythmia;
    b. acquiring an electrogram including a plurality of non-arrhythmic complexes;
    c. comparing the morphology of the non-arrhythmic complexes to the template; and
    d. deriving an indication of an impending arrhythmia as a function of the comparison between the plurality of non-arrhythmic complexes and the template.

8. The method of claim 7, wherein the plurality of non-arrhythmic complexes comprises a moving window such that as each new complex of the electrogram is acquired the oldest complex of a defined number of complexes in a sequence is removed from the sequence.

9. The method of claim 8, wherein said step of deriving an indication of an impending arrhythmia includes the step of calculating a parameter which is a summation of the results of each morphology comparison of the complexes within the window.

10. The method of claim 7, wherein the result of each morphology comparison is modified by a weighting factor.

11. The method of claim 10, wherein the weighting factor is a function of the duration of an immediately preceding inter-beat interval.

12. The method of claim 7, further including the step of determining if each complex is a premature ventricular contraction (PVC) and if it a complex is determined to be a PVC ignoring such complex for the comparing step.

13. A system for predicting cardiac arrhythmias for use in an implantable cardiac therapy device comprising:
    a sensor for acquiring an intracardiac electrogram including non-arrhythmic complexes; and
    a processor for acquiring a template representative of a normal sinus rhythm, for comparing the morphology of the non-arrhythmic complexes to the template, and for deriving an indication of an impending arrhythmia as a function of the comparison between the plurality of non-arrhythmic complexes and the template.

* * * * *